US00PP13223P3

(12) United States Plant Patent
Apps

(10) Patent No.: US PP13,223 P3
(45) Date of Patent: Nov. 12, 2002

(54) DAYLILY PLANT NAMED 'APRICOT SPARKLES'

(76) Inventor: Darrel A. Apps, 327 Beebe Run Rd., Bridgeton, NJ (US) 08302

( * ) Notice: Subject to any disclaimer, the term of this patent is extended or adjusted under 35 U.S.C. 154(b) by 29 days.

(21) Appl. No.: 09/808,319

(22) Filed: Mar. 15, 2001

(65) Prior Publication Data

US 2002/0133858 P1 Sep. 19, 2002

(51) Int. Cl.[7] ..... A01H 5/00
(52) U.S. Cl. ..... Plt./312
(58) Field of Search ..... Plt./312

*Primary Examiner*—Kent L. Bell
(74) *Attorney, Agent, or Firm*—Burns, Doane, Swecker & Mathis, LLP

(57) ABSTRACT

A new and distinct Hemerocallis hybrid cultivar of the dormant type named 'Apricot Sparkles' is provided. The new cultivar is very floriferous and forms attractive apricot colored blossoms with diamond dusting over an extended period of time that begins during late May to early June and commonly ends during late September to early October in U.S.D.A. Hardiness Zone No. 7A. The plant readily forms new fans (plants) and readily forms a number of scapes per fan. The new cultivar is particularity well suited for growing as distinctive colorful ornamentation in the landscape.

2 Drawing Sheets

BOTANICAL/COMMERCIAL CLASSIFICATION

Hemerocallis hybrid; Daylily.

VARIETY DENOMINATION

'Apricot Sparkles'.

SUMMARY OF THE INVENTION

The present invention comprises a new and distinct Hemerocallis hybrid cultivar of the dormant type, and hereinafter is referred to by the cultivar name 'Apricot Sparkles'.

The new cultivar is the product of a planned breeding program which had as its objective the creation of a distinctive new Daylily cultivar that is intended for use as attractive ornamentation in the landscape.

The cross that resulted in the production of the new cultivar of the present invention was carried out in a controlled environment during July, 1993, at Chadds Ford, Pa., U.S.A The female parent (i.e., the seed parent) was the 'Sunny Honey' cultivar (non-patented in United States) and the male parent (i.e., the pollen parent) was the 'Opportunity' cultivar (non-patented in the United States). The parentage of the new cultivar can be summarized as follows:

'Sunny Honey'×'Opportunity'.

The female parent displayed 8 to 9 cm golden yellow flowers, and the male parent displayed 8 to 9 cm light cream yellow (honey-colored) flowers.

Each of the parent of new cultivar is registered with the American Hemerocallis Society.

The seeds resulting from the above pollination were sown and small plantlets were obtained which were physically and biologically different from each other. A number of such plantlets were moved and transplanted to Bridgeton, N.J., U.S.A during early 1994. Selective study during the growing season of 1995 resulted in the identification of a single plant of the new and distinct cultivar of the present invention.

It was found that the new Hemerocallis hybrid cultivar of the present invention is of the dormant type and:

(a) Forms attractive apricot colored flowers with diamond dusting whereby the blooms glisten and sparkle in the sunlight and have substantial substance and a flat slightly recurved form,
(b) Displays a long blooming season with substantially conitnuous blooming,
(c) Exhibits a propensity to readily form a plurality of fans, and
(d) Readily forms a plurality of scapes per fan over the flowering season.

The 'Apricot Sparkles' cultivar resembles well-known culitvars, such as the 'Stella De Oro' cultivar (non-patented in the United States) and the 'Happy Returns' cultivar (non-patented in the United States) in the sense that it commonly possesses an extremely long and substantially continuous blooming season of up to approximately 125 days in U.S.D.A Hardiness Zone No. 7A. Such blooming commonly begins during late May to early June and commonly ends during late September to early October. This compares to a bloom period of less than 30 days for most of the hybrid Daylilies that are presently available.

As indicated, 'Apricot Sparkles' exhibits attractive apricot colored flowers with diamond dusting that readily can be distinguished from the orange-yellow flowers of the 'Stella De Oro' cultivar and the medium yellow flowers of the 'Happy Returns' cultivar. Also, neither the 'Stella De Oro' cultivar nor the 'Happy Returns' cultivar display noticeable diamond dusting. To the best of the knowledge of the originator, 'Apricot Sparkles' is the first long and substantially continuous blooming Daylily having flowers that exhibit an apricot hue combined with diamond dusting. Such diamond dusting characteristic is discussed in the literature and is believed to be brought about by a superfluity of dye-enhancing agents, which are themselves colorless, belonging to a group of organic chemicals called flavonoids. Such effect commonly eludes depiction in a photograph but is readily apparent to the eye when the blossoms are exposed to direct sunlight.

The new cultivar has been observed to form up to 10 new fans per year. This compares to approximately 6 to 8 fans per year for the 'Stella De Oro' cultivar and the 'Happy Returns' cultivar. Most Daylily cultivars from only approximately 2 to 3 fans per year. Also, the new cultivar commonly forms 2 to 4 scapes per fan during the flowering season, unlike most Daylilies that commonly produce only one scape per fan.

Asexual reproduction of the cultivar by divison was initially carried out during September, 1995 at Bridgeton, N.J., U.S.A. At the time of such asexual reproduction the original plant of the new cultivar consisted of a clump of twenty fans that were phenotypically identical to each other. More specifically, the clump of the new cultivar was removed from the field and the fans were divided. It has been demonstrated that the characteristics of the new culitvar are firmly fixed and are well retained following such asexual reproduction.

'Apricot Sparkles' has not been observed under all possible environmental conditions to date. Accordingly, it is possible that the phenotype may vary somewhat with variations in the environment, such as temperature, light, day length, contact with pesticides, etc.

BRIEF DESCRIPTION OF PHOTOGRAPHS

The accompanying photographs were prepared during the late August to early September 2000 time period, and show as nearly true as it is reasonably possible in a color illustration of this character the original plant and flowers of the new cultivar of the present invention. The plant is being grown outdoors in the field at Bridgeton, N.J., U.S.A.

DETAILED DESCRIPTION

The chart used in the identification of colors described herein is The R.H.S. Colour Chart of The Royal Horticultural Society, London, England. In some instances, more common color terms are provided and are to be accorded their usual dictionary significance. The original plant of the new cultivar is described when observed during early September 1996 while growing at Bridgeton, N.J., U.S.A. under field growing conditions.

Figure 1:
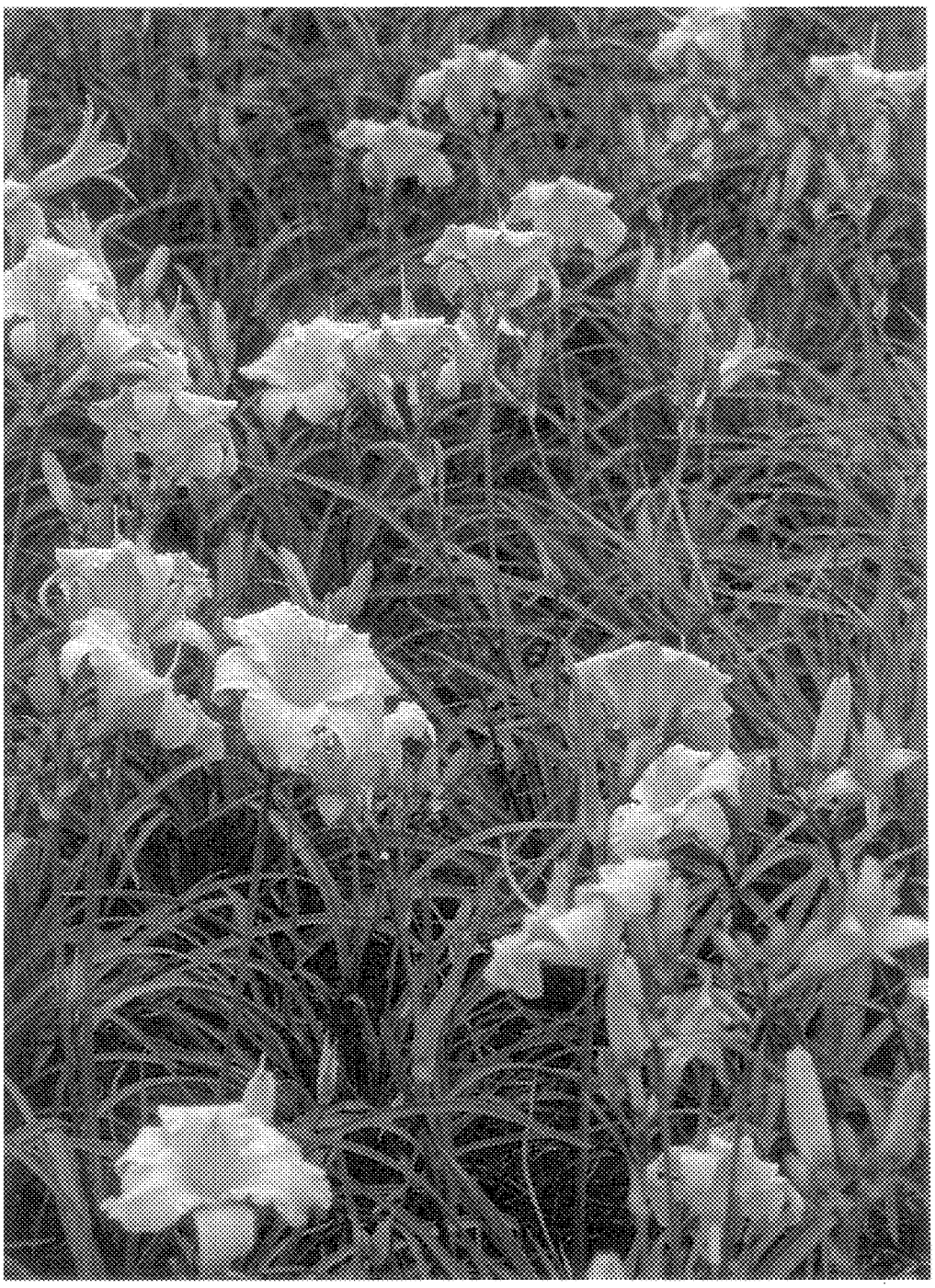
FIG. 1 illustrates the plant clump with foliage, buds and flowers in various stages of maturity.
Figure 2:
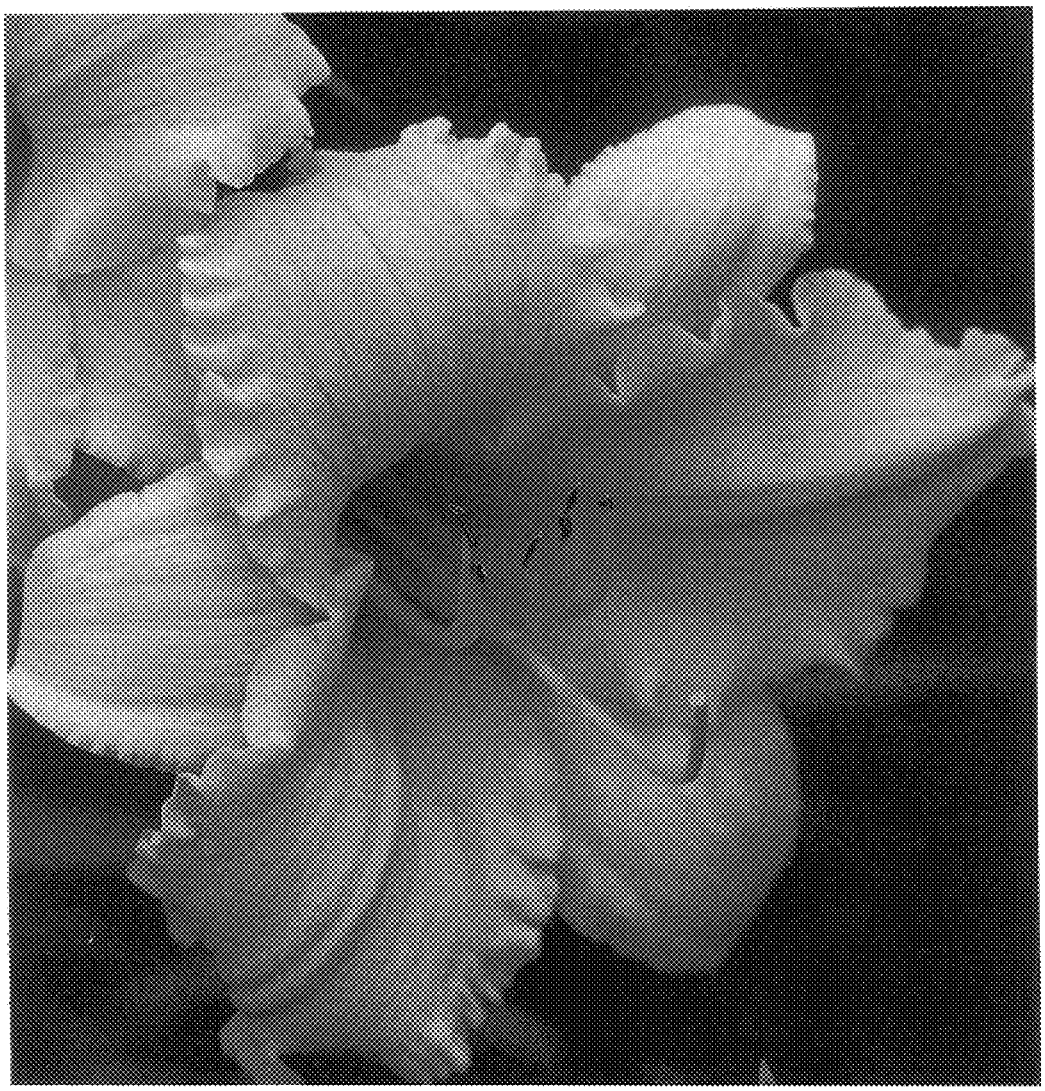
FIG. 2 illustrates a close up view of a mature flower of the present invention wherein the stamens and pistil are visible. It is not possible to photographically depict the diamond dusting characteristic whereby the blooms glisten and sparkle in direct sunlight.

Plant:

*Foliage.*—Form: Single stem, substantially erect scapes from a fan-shaped plant having narrow arching, long, keeled, grass-like glabrous leaves that are two-ranked at the base of the scape. Quantity: abundant, with a mature plant commonly having approximately 12 to 14 leaves per fan. Leaf Size: Commonly approximately 1.3 cm in width on average and approximately 31 cm in length on average. Leaf Shape: linear and long-keeled (as illustrated in FIG. 1) with entire margins. Texture: glabrous. Color: medium green, Yellow-Green Group 146A. Type: dormant with the plant losing all of its foliage during the winter.

*Scape.*—Color: Lettuce Green, Yellow-Green Group 144A. Height: commonly approximately 40 cm on average.

*Disease resistance.*—Typical of Hemerocallis with no problems having been observed to date.

Inflorescence:

*Bud.*—Form: modified oblanceolate (as illustrated in FIG. 1). Size: on the day prior to opening commonly approximately 5 cm in length on average and approximately 1.2 cm in width on average. Opening Rate: commonly approximately three hours on average. Outer Tepal Color: When outer tepals first divide, Lettuce-Green, Yellow-Green Group 144A. Peduncle Character: rigid and sturdy. Peduncle color: medium green, Green Group 138A.

*Flower.*—Size: Commonly has a diameter of approximately 10 cm on average and a depth of approximately 5 cm on average. Borne: singly on the branchlets of a sturdy erect rachis which is ramulose. Each scape commonly has at least three peduncles, each of which divides into approximately ten pedicles. Blooms Per Scape: commonly ranges form 1 to 2 each day. Tepalage: each flower consists of six perianth segments wherein there are three outer tepals and three inner tepals all in an imbricated arrangement. Outer Tepal Shape: oblancecolate with slightly undulated entire margins and an acuminate apex. Outer Tepal Texture: ribbed. Outer Tepal Size: commonly approximately 6 cm in length on average and approximately 2.5 cm in width on average. Outer Tepal Color: apricot, Orange Group 24B (both surfaces). Coloration fades to lighter than orange Group 24B as the flower ages then becomes darker than Orange 24B at senescence. Ventation is darker than Orange Group 24B (both surfaces). Inner Tepal Shape: broadly obovate with entire undulated margins and a broadly cuspidate apex. Inner Tepal Texture: slightly puckered and ribbed and having a diamond dusting whereby the blooms glisten and sparkle in direct sunlight. Inner Tepal Size: commonly approximately 6 cm in length on average and approximately 5 cm in width on average. Inner Tepal Color: apricot, Orange Group 24B (Both surfaces). Blooming Habit: the flowers commonly bloom substantially continuously and the scapes commonly are substantially continuously in bloom for up to approximately 125 days per year in U.S.D.A. Hardiness Zone No. 7A. Based on the parentage and observations of the new cultivar to date it has been shown to perform satisfactorily in U.S.D.A. Hardiness Zone Nos. 4 through 8. Effects of Weather: the flowers will withstand rain damage in view of the strength of the tepals. Lasting Quality: commonly at least 16 hours. As with other Hemerocallis cultivars, the flower coloration eventually fades somewhat during the day with the natural effects of the environmental conditions and ongoing maturity. Fragrance: slight.

*Reproductive organs.*—Stamen Number: six per flower. Stamen Disposition: individually inserted at the summit of the perianth tube. Anther Disposition: introrse. Anther Size: approximately 0.8 cm in length. Anther Color: Grey-Brown Group 199B. Filament Configuration: slender. Filament Length: commonly approximately 4 cm on average. Filament Color: apricot, Orange Group 24B. Pollen Color: Yellow Group 6C. Pistil Number: one per flower. Style Length: approximately 5 cm in length on average. Style Color: apricot, Orange Group 24B. Stigma Color: Yellow Group 6C. Ovaries: three-celled, oblong, and becoming a loculicidal three-valved capsule.

*Fruit.*—Configuration: the seed pod is in the form of an ovoid capsule. Color: at maturity commonly ranges between Yellow-Green Group 144A and Greyed-Green Group 197B. Fertility: the seeds are fertile.

I claim:

1. A new and distinct cultivar of Hemerocallis hybrid plant of the dormant type, substantially as herein shown and described, which:

(a) forms attractive apricot colored flowers with diamond dusting whereby the blooms glisten and sparkle in the sunlight and have substantial substance and a flat slightly recurved form, (b) displays a long blooming season with substantially continuous blooming, (c) exhibits a propensity to readily form a plurality of fans, and (d) readily forms a plurality of scapes per fan over the flowering season.

* * * * *